United States Patent [19]
Korb et al.

[11] Patent Number: 5,738,856
[45] Date of Patent: Apr. 14, 1998

[54] SKIN CARE PREPARATION AND METHOD

[75] Inventors: Donald R. Korb, Boston, Mass.; Thomas Glonek, Oak Park, Ill.; Jack V. Greiner, Winchester, Mass.

[73] Assignee: Ocular Research of Boston, Inc., Boston, Mass.

[21] Appl. No.: 552,426

[22] Filed: Nov. 3, 1995

[51] Int. Cl.⁶ .................................................. A61K 7/48
[52] U.S. Cl. .................... 424/401; 514/844; 514/861; 514/863; 514/864; 514/937
[58] Field of Search ...................... 424/401; 514/844, 514/861, 863, 864, 937

[56] References Cited

U.S. PATENT DOCUMENTS

| | | | |
|---|---|---|---|
| 4,661,343 | 4/1987 | Zabotto et al. | 424/59 |
| 4,914,088 | 4/1990 | Glonek et al. | 514/76 |
| 5,085,856 | 2/1992 | Dunphy et al. | 424/64 |
| 5,278,151 | 1/1994 | Korb et al. | 514/76 |

OTHER PUBLICATIONS

Rawlings, A.V., "Skin Waxes: Their Composition, Properties, Structures and Biological Significance", *Waxes: Chemistry, Molecular Biology and Functions*, Unilever Research, Colworth House, Bedford, United Kingdom, pp. 223–259.

*Primary Examiner*—Jyothsan Venkat
*Attorney, Agent, or Firm*—Robert L. Goldberg

[57] ABSTRACT

A composition and method for treatment of skin. The composition comprises a pharmaceutically acceptable carrier containing a bilayer component having one or more polar terminus groups and one or more non-polar terminus groups separated from said polar terminus groups capable of penetrating the outer surface of the skin to form an aligned bilayer within the stratum corneum. The bilayer assists in the formation of bilayer lamellae that is believed to replicate the bilayer lamellae present in healthy skin. The composition is topically applied to the skin as often as is required.

18 Claims, 2 Drawing Sheets

SKIN CARE PREPARATION AND METHOD

INTRODUCTION

This invention relates to treatment of skin disorders. More particularly, this invention, by transport of certain polar lipids, promotes and maintains epidermal lipid lamellae within the intercellular spaces between corneocytes.

DESCRIPTION OF THE PRIOR ART

A primary function of the skin is to provide a protective barrier for the body. For example, it provides mechanical protection to the body's outer tissues, acts as a barrier against penetration of chemicals and microorganisms from the external environment and prevents evaporation of water from the body. With regard to evaporation of water, the average area of the skin of an adult is about 2 meters$^2$, but water evaporation through this large surface area is only about 300 grams per day. Control of water evaporation is perhaps the most important function of the skin. Without this water barrier, the body would not survive.

The outer layer of the skin, the epidermis, is composed of four main cellular layers. The stratum basale is the proliferating component of the epidermis where the columnar-shaped stem cells provide a progeny of daughter cells which migrate to the surface layers of the skin. The stratum spinosum comprises the differentiation-committed polyhedrally shaped cells exhibiting a spiny appearance due to the presence of a large number of desmosomes, which are macromolecular complexes of adhesion proteins, desmoplakins, desmogleins and desmocollin which mediate cohesion with adjacent cells. The stratum granulosum comprises flattened polygonally shaped cells exhibiting a variety of differentiation, specific products inclusive of the lipid-filled membrane coating granules and the keratohyalin granules rich in the natural-moisturizer precursor protein, profilaggrin. Finally, the stratum corneurn is the impermeable epidermal outer cellular layer composed of flattened densely packed anucleate cells or corneocytes, separated by a lameliar matrix of complex intercellular lipids, the bulk of which are classified as polar lipids.

The stratum corneum is the outermost cellular layer of the epidermis and is the layer that functions as a protective barrier between the body and its environment. The stratum corneurn is made up of corneocytes extracellularly separated from each other by lamellae composed of multiple lipid bilayers. In general, the composition of the surface stratum corneum lipids is a mixture of sebaceous-gland-derived and epidermally-derived lipids. Stratum corneum lipids comprise ceramides in predominant amount, fatty acids, cholesterol, cholesterol sulfate, minor amounts of phospholipids and glucosyl ceramides.

The lipid bilayers located in the intercellular spaces separating the corneocytes have a lameliar structure. It is believed that each bilayer comprises an aligned array of molecules having hydrophilic terminus groups and hydrophobic terminus groups separated from each other by a molecular spacer. It is further believed that an aqueous layer is interdigitated along the aligned hydrophilic polar head groups and an oily lipid layer may be interdigitated along the hydrophobic terminus groups. Regardless of its structure, the lameliar array of bilayers is essential to provide lubricity between corneocytes and to maintain the entire stratum corneum soft and supple. A discussion of the composition of the epidermis and the role of lipids can be found in Larsson, *Lipids-Molecular Organization, Physical Functions and Technical Applications*, The Oily Press, Limited, Scotland, 1994, Chapter 11; Hamilton, *Waxes: Chemistry, Molecular Biology and Functions*, The Oily Press, Limited, Scotland, 1995, Chapter 6; and Fitzpatrick, et al, *Dermatology in General Medicine*, McGraw-Hill, Inc., New York, 1993, Volume 1, Chapter 14, each incorporated herein by reference.

There are many instances when the stratum corneum is compromised resulting in evaporation and loss of water from this layer. This can result as a consequence of continuing low humidity; excessive exposure to sun; perturbation and disruption of the superficial layer of the epidermis by puncture or abrasion; the action of solvents on the skin such as detergents and organics such as paint removers; aging; diet, especially in the absence of essential fatty acids; excessive washing; and skin scaling disorders such as psoriasis, ichthyosis and atopic eczema. When evaporation of water from the epidermis occurs, the separation between corneocytes decreases resulting in a loss of lubrication between the corneocytes and the flaking of skin fragments or cells from the affected area. This condition is uncomfortable, considered aesthetically unattractive and opens a pathway for infection.

A wide range of skin care formulations suitable for topical delivery are available for the treatment of dry and flaking skin. One class of skin care formulation provides a protective layer over the stratum corneum without penetrating the stratum corneum and without chemically influencing the skin. Evaporation of water is reduced using these formulations as they provide a protective layer over the skin. Examples of protective formulations include pigment formulations, formulations containing sun-screening agents and skin protection creams. Further examples of such formulations are disclosed in U.S. Pat. Nos. 4,309,448; 4,534,981 and 4,661,343, each incorporated herein by reference. Since these formulations are not designed to penetrate the skin, they do not augment the dehydrated lamellae and thus do not provide lubrication between corneocytes. Another class of skin care formulation involves penetration of water and active components through the skin, mainly designed to lubricate and moisturize the stratum corneum. These formulations utilize an osmotic driving force for water transport from the air-skin interface to the stratum corneum by adding materials such as glycerol, sugars, lactic acid and amino acids or urea. Further examples of such formulations are disclosed in U.S. Pat. Nos. 4,971,800; 5,045,317 and 5,051,317, each incorporated herein by reference. The two classes of formulations are known as "external" and "penetrating" formulations, respectively.

Problems are associated with each of the external and penetrating skin care formulations. The external formulations do not carry active components into the stratum corneum and consequently do not replenish nor influence the lamellae separating the corneocytes. The penetrating formulations carry active components into the stratum corneum, but the components carried into this layer do not remedy deficiencies in the lamellae. Moreover, the components penetrate into and through the stratum corneum deeper into the epidermis without a prolonged residence time in the stratum corneum. Consequently, both the external and penetrating skin care formulations fail to provide extended lubrication between corneocytes, fail to repair the intercellular lamellae and fail to remedy the dry skin condition.

SUMMARY OF THE INVENTION

The present invention is directed to a topical treatment composition for skin disorders. The composition comprises a compound in a pharmaceutically acceptable carrier for topical delivery that penetrates the epithelial surface into the stratum corneum to provide prolonged lubrication and moistening. The invention is predicated upon the discovery that to provide prolonged lubrication and moistening of the skin, it is desirable to artificially replicate and replenish the bilayer lamellae naturally occurring in healthy skin.

In accordance with the invention described herein, a topical treatment formulation is provided comprising a pharmaceutically acceptable topical carrier containing a non-toxic compound having one or more polar terminus groups and one or more non-polar terminus groups where the polar and non-polar groups are separated from each other by a spacer segment. For purposes of convenience, this compound will be referred to from time to time as the "bilayer component". The composition also desirably contains a neutral lipid.

The bilayer component is a compound capable of forming lamellae (multiple bilayers) separated from each other by a water layer within the epidermis, probably within the stratum corneum. Especially suitable bilayer components for formation of the lameliar are phospholipids and triglycerides dispersed in aqueous media because such materials form the desired bilayer and are normally found in healthy skin. Thus the materials are non-toxic and safe for human use.

Without wishing to be bound by theory, it is believed that the bilayer component of the skin care formulation enhances formation of multiple bilayer structures within the stratum corneum which would naturally occur in healthy skin. It is further believed that each bilayer comprises an aligned array of molecules formed from the bilayer component where the non-polar terminus groups of each layer of the bilayer are aligned with each other and the polar terminus groups of the bilayer extend outward from the bilayer film. Lamellae of bilayers are formed by the polar groups of one bilayer aligning with the polar groups of another bilayer through an intermediate aqueous layer. The laminar structure so formed, from top to bottom, appears as a lipid bilayer on top of a water layer on top of a lipid bilayer, etc. until the entire space between corneocytes is filled. It is further believed that the top and bottom layers of the lamellae bond to the cornified epithelial cells by hydrogen bonding thus providing stability to the entire structure and long lasting moisturizing of the skin. Finally, it is believed that when a neutral lipid is contained within the treatment composition, the neutral lipid forms an aligned layer between the non-polar groups of the bilayer thus providing greater lubricity between corneocytes.

The above hypothesized structure is believed to replicate the lameliar structure normally found in healthy skin. Consequently, the skin care formulations of the present invention are suitable for treatment of skin, whether human or animal, to provide long lasting remedial treatment of dry skin, irritation and other skin maladies. The skin care formulation is especially useful for treatment of irritated periocular skin.

DESCRIPTION OF THE PREFERRED EMBODIMENTS

Figure 1:
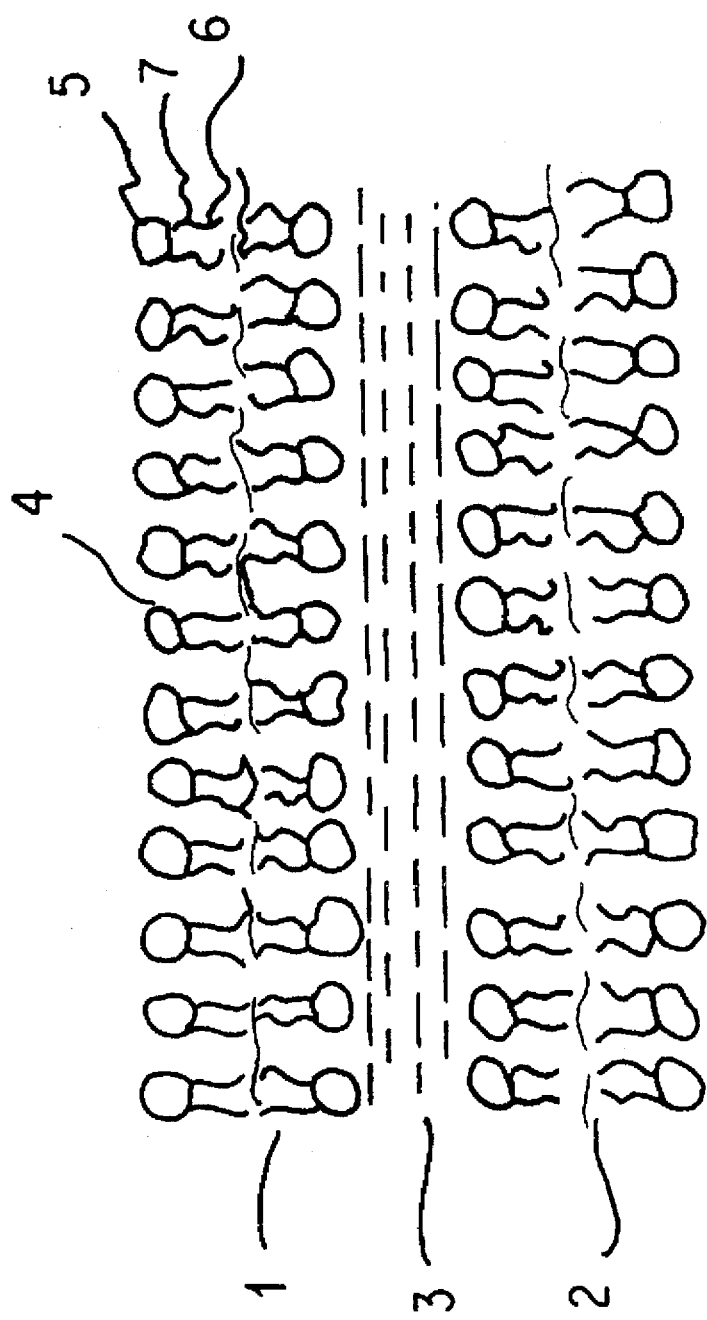
FIG. 1 is a pictorial representation of bilayers formed in accordance with the invention.

As described above, a major component of the treatment composition of the invention is a bilayer component—a non-toxic compound having at least one hydrophobic terminus group and at least one hydrophilic terminus group, where the groups are separated from each other by a spacer segment. The bilayer component forms an organized, aligned bilayer structure within the epidermis, most likely within the stratum corneum, where adjacent bilayers are separated by a water layer. The bilayer structure is pictorially represented in FIG. 1 of the drawings wherein there is represented two bilayers, 1 and 2, respectively, each separated from the other by a layer of water 3. Each bilayer comprises an aligned array of molecules 4 formed from the bipolar component of the treatment composition. Each molecule has a terminus hydrophilic head group 5, a terminus hydrophobic group 6, and a spacer 7 therebetween. The terminus hydrophobic group may be a portion of the spacer segment such as the last one or more methyl groups in a long chain hydrocarbon.

Preferred bilayer components of the skin care composition are those materials that form bilayers approximating those found naturally in healthy skin and which carry a net negative charge. By use of materials naturally found in the skin, problems of incompatibility with the skin are avoided. The result of applying a skin care composition containing such a component to the skin is to artificially replicate that which should be found in healthy skin. By use of a material having a net negative charge, the bilayer component rapidly penetrates the skin to form the desired lamelar structure.

Phospholipids comprise one class of bilayer component material suitable for use in the subject skin care compositions. Exemplary phospholipids are represented by the following formula:

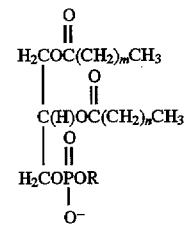

where m and n are whole integers varying between about 8 and 24 and R represents a moiety esterified to the phosphoric group which determines the specific phospholipid compound used. Thus R may be a polyol, an amine, hydrogen, a hydroxylated carboxylic acid, a sugar, a quaternary amine, an amino-acid-substituted glycerol, a phosphorylated sugar, a phosphorylated polyol, a sulfated sugar, a sulfated polylol, an acylated sugar, and an acylated polyol.

Phospholipids are well-known to those skilled in the art and a discussion of phospholipids can be found in Lehninger, *Biochemistry*, 2 Ed., Worth Publishers, New York, pp. 279–306; Kirk-Othmer, *Concise Encyclopedia of Chemical Technology*, John Wiley and Sons, New York, pp. 458–459, 1985. As is known in the art, the phospholipids differ in size, shape and the charge of their polar head groups. They may be negatively charged, positively charged or neutral. Of the phospholipids, the negatively charged phospholipids are preferred.

Phosphoglycerides are negatively charged phospholipids and comprise the most preferred bilayer component. The phosphoglycerides are compounds where one primary hydroxyl group of glycerol is esterified to phosphoric acid and the other two hydroxyl groups are esterified with fatty acids. The parent compound of the series is therefore the phosphoric acid ester of glyceroh This compound has an asymmetric carbon atom and therefore, the term phosphoglycerides includes stereoisomers. All phosphoglycerides have a negative charge at the phosphate group at pH 7, and the $pK_a$ of the phosphate group is in the range of 1 to 2. The head groups of phosphatidyl inositol, phosphatidyl glycerol including diphosphatidyl glycerols (having the common name cardiolipins) and the phosphatidyl sugars have no electric charge. All are polar because of their high hydroxyl group content. Because of the negative charge of the phosphate group and the absence of a charge in the head group, the net charge of each of these materials is negative. Likewise, the head group of phosphatidyl serine contains an alpha-amino group ($pK_a$ of 10) and a carboxyl group ($pK_a$ of 3). Therefore, the molecule contains 2 negative charges and 1 positive charge at pH 7 giving it a net negative charge.

Complex phospholipids having a net positive charge are also within the scope of the invention but are lessor preferred because of the price and scarcity of these materials. Examples of positively charged complex phospholipids within the scope of the invention are those containing the basic acyl amino acid groups. Such compounds are a subgroup within the family of the o-aminoacylphosphatidylglycerols.

Phospholipid head groups such as ethanolamine in phosphatidylethanolamine have a positive charge at pH 7 and thus, these two phosphoglycerides are dipolar zwitterions with no net charge. Such compounds may also be used in accordance with the invention.

As is known to those skilled in the art, phospholipids are available from a variety of sources such as egg yolks, soy beans, etc. One form of phospholipid commercially available is sold under the trade designation lecithin. These sources of phospholipid typically contain a mixture of components including neutral lipids as exemplified by glycerides, cholesterol and cholesterol esters; phospholipids having a net charge of zero exemplified by phosphatidyl choline, phosphatidyl ethanolamine; various unsaturated and saturated fatty acids; and charged phospholipids such as phosphatidyl glycerol, phosphatidyl inositol and phosphatidic acid. The charged phospholipids are typically contained in these naturally occurring products in varying concentration, typically varying from about 1 percent up to 100 percent of the total concentration dependent upon the source and extraction procedures used.

Another class of materials suitable for formation of the bilayer are the neutral, but polar glycerides, particularly triglycerides. Glycerides are esters of glycerol and fatty acids. The preferred glycerides for use as the bilayer component for preparation of a skin care composition are the triglycerides represented by the following general formula:

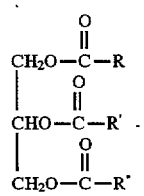

where each of R, R' and R" is a fatty acid residue. The fatty acid may have from 14 to 28 carbon atoms and exemplary fatty acids that may be esterified with glycerol to form a mono, di-or triglyceride include myristic acid, palmitic acid, palmitoleic acid, stearic acid, oleic acid, linoleic acid, linolenic acid, ricinoleic acid, gadoleic acid, arachidonic acid, behenic acid, cetoleic acid and erucic acid.

Sources of the fatty acids used for formation of glycerides are oils and fats such as coconut oil, palm oil, animal fat, olive oil, peanut oil, sunflower oil, cottonseed oil, linseed oil, castor oil, marine fats, rapeseed oil, etc. Such materials are well-known in the art.

Both the phospholipids and the glycerides may be used alone or in combination with each other in the preparation of the skin care formulation. Because these materials are naturally occurring materials in normal skin, they may be applied to the skin without concern for adverse reaction. Moreover, because these materials possess polar head groups, they seek water thus creating a driving force causing the phospholipids and glycerides to penetrate the epidermis and form a bilayer structure within the stratum corneum. The phospholipids carrying a net negative charge penetrate the skin at a substantially greater rate than the triglycerides.

In addition to the bilayer component, it is desirable to include a neutral lipid in the skin care composition of the invention. Without wishing to be bound by theory, it is believed that the neutral lipid forms a layer 6 (FIG. 1) aligned along the non-polar terminus groups of the bilayer. This layer is believed to further enhance lubricity between corneocytes as well as assisting in the prevention of water evaporation from the skin. Typical neutral lipids suitable for purposes of the invention include polyisoprenes, steroids such as cholesterol, waxes and other monoesters, cholesterol esters and other sterol esters and synthetic alkanes derived from man-made polymerization processes, and silicon containing oils such as simethacone. The preferred neutral lipid is an oil, most preferably a non-polar oil.

As is known in the art, oils may be derived from animals, plants, nuts, petroleum, etc. Those derived from animals, plant seeds, and nuts are similar to fats and consequently, contain a significant number of polar acid and/or ester groups and therefore, lesser preferred for purposes of this invention. Alternatively, oils derived from petroleum are usually aliphatic or aromatic hydrocarbons that are essentially free of polar substitution and therefore are preferred for purposes of the present invention provided the oil is refined so as to be compatible with human tissue. Most preferably, the oil is a hydrocarbon oil having from 10 to 50 carbon atoms, especially an oil that is a saturated n-alkane or isoalkane hydrocarbon having from 14 to 26 carbon atoms. Unsaturated alkene hydrocarbons may be used but are less chemically stable as the double bonds tend to oxidize.

Figure 2:
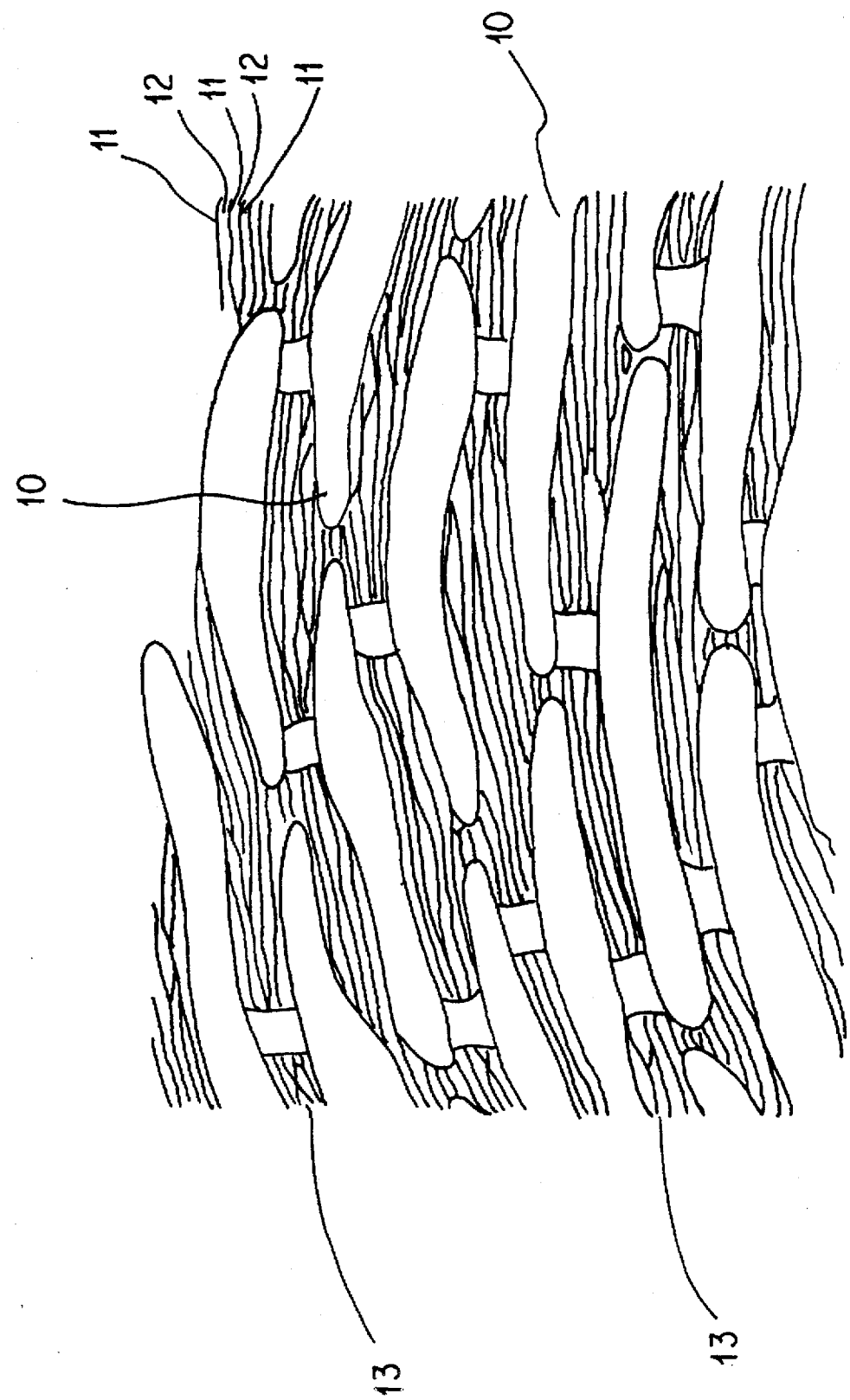
FIG. 2 is a pictorial representation of skin having been treated with the skin care formulation of the subject invention where bilayer lamellae are formed within the stratum corneum.

Following topical application of a treatment composition to the skin in accordance with the invention, lamellae between corneocytes are believed to form as pictorially represented in FIG. 2 of the drawings. In FIG. 2, there is shown corneocytes 10 separated by lamellae comprising a plurality of bilayers 11 separated by aqueous layers 12. The lamellae comprising the bilayers and aqueous layers are more clearly shown in FIG. 1 of the drawings as described above. It can be seen that the lamellae fill the space between corneocytes thus providing lubricity. Rigidity is added to the structure by naturally occurring ceramides 13 which bind the corneocytes together and thereby prevent flaking of skin fragments from the surface of the skin. It is believed that neutral lipid layers (not shown in the drawing) are also present in the bilayer formation aligned along the hydrophobic ends of the bilayer as previously described.

The bilayer component and neutral lipid of the skin care composition can be topically applied as a mixture directly to the skin with beneficial result. However, materials of this nature typically have a consistency ranging from a viscous fluid to a thick, highly viscous semi-solid. In this form, the components are aesthetically unappealing and an oily layer is formed on the skin that slowly diffuses into the skin. Consequently, it is desirable that the materials be contained in a topical skin lotion base or carrier. Topical carriers are known to refer to carrier materials suitable for topical application of drugs or cosmetics to the skin and contain materials known in the cosmetic and medical arts, e.g., any liquid or non-liquid carrier, gel, cream, ointment, lotion, emulsifier, solvent, liquid diluent, or the like, which does not adversely affect living animal tissue or interact with other components of the composition in a deleterious manner.

Specific materials that may be used as carriers include water, liquid alcohols, liquid glycols, liquid polyalkylene glycols, liquid esters, liquid amides, liquid protein hydrosylates, liquid alkylated protein hydrosylates, liquid lanolin and lanolin derivatives, and other like materials. Exemplary carriers include water, alcohols inclusive of both monohydric and polyhydric alcohols, e.g. ethanol, isopropanol, glycerol, sorbitol, 2-methoxyethanol, diethylene glycol, ethylene glycol, hexylene glycol, mannitol, cetyl alcohol and propylene glycol; ethers such as diethyl or dipropyl ether; polyethylene glycols and methoxypolyoxyethylenes; carbowaxes having molecular weights ranging from 200 to 20,000; polyoxyethylene glycerols; polyoxyethylene; sorbitols; and stearoyl diacetin. The topical carriers preferably include both alcohol and water so as to accommodate lipophilic and hydrophilic components.

In addition to the above, topical carriers typically include other agents and ingredients commonly employed in dermatological and cosmetic ointments and lotions. For example, pH adjustors and buffers such as sodium hydroxide, sodium citrate or tetrasodium EDTA; excipients; fragrances such as menthol; opacifiers such as zinc oxide, magnesium aluminum silicate and titanium dioxide; preservatives such as dichlorobenzyl alcohol, benzoic acid, methylparaben and phenyl carbinol; antioxidants; gelling agents such as petrolatum and mineral wax; thickening agents such as carboxymethylcellulose; stabilizers; surfactants; emollients; coloring agents and the like may be present in the carrier.

The bilayer component and neutral lipid may be added to a skin care product that serves an additional purpose. Such materials could include sunblocks, sunscreens, conventional moisturizers, etc. Alternatively, the components may be applied to the skin as an aerosol or in any other form as would be apparent to those skilled in the art.

In preferred embodiments of the invention, the bilayer component and the neutral lipid are applied to the skin in a topical carrier that is in the form of an aqueous oil in water emulsion or in the form of a cream or lotion.

The compositions of the invention may also include a pharmacologically active agent or drug known to the art to mean any chemical material or compound suitable for topical or topical administration which induces any desired local or systemic affect. Such substances include the broad classes of oil or water soluble compounds normally delivered through body surfaces and membranes, including skin. In general, this includes therapeutic agents in all of the major therapeutic areas including, but not limited to, anti-infectives such as antibiotics and antiviral agents; analgesics and analgesic combinations; anorexics; antiarthritics; anti-asthmatic agents; anticonvulsants; antidepressants; antidiabetic agents; antidiarrheals; antihistamines; antiseptics; anti-inflammatory agents; antimigraine preparations; antimotion sickness agents; antinauseants; antineoplastic agents; antiparkinsonism drugs; antipruritics; antipsychotics; antipyretics; antispasmodics, including gastrointestinal and urinary; anticholinergics; sympathomimetics; xanthine derivatives; cardiovascular preparations, including calcium channel blockers, beta-blockers; antiarrhythmics; antihypertensives; diuretics; vasodilators, including general coronary, peripheral and cerebral; central nervous system stimulants; cough and cold preparations; decongestants; diagnostics; hormones; hypnotics; immunosuppressives; muscle relaxants; parasympatholytics; psychostimulants; sedatives, tranquilizers, anesthetics, vitamins and combinations of the above. The amount of the pharmacologically active agent is an effective amount defined as a non-toxic but sufficient amount of a compound to provide the desired local or systemic effect and performance at a reasonable benefit/risk ratio attending any medical treatment.

In addition, the topical carrier may include a penetration enhancer defined as a material that increases the permeability of the skin to one or more active agents so as to allow for cutaneous delivery of a pharmacologically active agent. Various compounds for enhancing the permeability of skin are known in the art. For example, U.S. Pat. Nos. 4,006,218, 3,551,554 and 3,472,931, respectively describe the use of dimethylsulfoxide (DMSO), dimethyl formamide (DMF) and N,N-dimethylacetamide (DMA) to enhance the absorption of topically applied materials through the stratum corneum. Other compounds which have been used to enhance skin permeability include decylmethylsulfoxide ($C_{10}MSO$), polyethylene glycol monolaurate (PEGML; see, e.g., U.S. Pat. No. 4,568,343), and the 1-substituted azacycloheptan-2-ones, particularly 1-n-dodecylcyclazacycloheptan-2-one (available under the trademark "Azone" from Nelson Research & Development Co., Irvine, Calif.; see U.S. Pat. Nos. 3,989,816, 4,316,893 and 4,405,616). Other additives could comprise hyperosmolar and hypoosmolar agents.

As described herein, the skin care composition of the invention preferably comprises the combination of a bilayer component and a neutral lipid contained within a topical carrier. The concentration of the bilayer component may vary within wide limits and broadly, is used in an amount sufficient to replicate that lamellar structure found within healthy skin. In general, this amount may vary between 0.05 and 35 of the percent by weight of the total composition and more preferably varies between 1.0 and 25 percent of the composition. The neutral lipid component may be included in the composition within a wide range of concentration and preferably varies between 0.1 and 35 percent by weight of the total composition and more preferably, varies between 1.0 and 10 percent of the composition.

The skin care composition of the invention is used to treat the skin in essentially the same manner as a conventional skin moisturizer. The composition is rubbed onto the skin at least once daily and more preferably, twice daily in the morning and evening. More severe skin disorders may require more frequent application. Dependent upon the topical carrier used, the composition is typically applied to the skin in an amount sufficient to cover the effected area and form a thin coating over the skin. Excessive amounts are not necessary. The composition gradually passes into the skin, typically within a period of from one to ten minutes, again dependent upon the topical carrier used.

The invention will be better understood by reference to the following examples. In each examples, one of the two following formulations were used. In the emulsion formulation, the phospholipid concentration is lower than desired and better results would be expected with an increased concentration of the phospholipid.

Emulsion Formulation

| Component | Concentration (Weight %) |
| --- | --- |
| Dimyristylphophatidyl glycerol | 0.05 |
| Mineral Oil (Drakeol 35) | 10.00 |
| Polyoxyl 40 stearate (Myrj 52) | 0.15 |
| Ethylenediaminetetraacetic acid | 0.10 |
| Sodium chloride | 0.67 |
| Water | balance |
| pH | 6.94 |

Cream Formulation

| Component | Concentration (Weight gm) |
| --- | --- |
| Cream vehicle | |
| Isopropyl palmitate | 8.0 |
| Cetyl alcohol | 0.8 |
| Stearyl alcohol | 1.0 |
| Bees wax | 0.4 |
| Stearic acid | 2.0 |
| Glycerol monostearate | 2.0 |
| Sodium hydroxide | 0.4 |
| Myristyl myristate | 2.4 |
| Propylene glycol | 8.0 |
| Benzyl alcohol | 0.6 |
| Methyl-propyl paraben mixture | 0.4 |
| Carbopol 934 | 0.6 |
| Oleic acid | 2.6 |
| Arlacel-60 | 1.6 |
| Tween 60 | 2.4 |
| Water | to 100 |
| Hydrogenated triglycerides | 30.00 |

EXAMPLE 1

Diagnosis: Angular blepharitis.

History: Chronic redness at outer angles of both eyelids for past five years.

Physical Appearance of Affected Area: Temporal canthi of both eyes (the junction of both lids at the temporal side) red and inflamed with usual scaling present. Also cracks and fissures present in the skin at the temporal canthi and in the groove extending from the canthi of both eyes.

Prior Treatment: Creams not effective. Synalar (asteroid) used with success but condition constantly reoccurred.

Treatment Regime: Cream formulation used in small amounts and rubbed onto affected areas three times per day.

Results: Fifty percent improvement in two weeks, seventy five percent improvement in three weeks and ninety percent improvement in four weeks.

Comment: Subject did not wish to use prior medication as a control on one side since only steroids were effective and whereas the continual use of steroids were thought to cause thinning of the skin.

EXAMPLE 2

Diagnosis: Angular blepharitis.

History: Ocular condition—severe keratoconus complicated by meibomian gland dysfunction which resulted in foam. The foam is apparently the result of fatty acid formation which alters the skin at the external temporal canthi resulting in angular blepharitis and in the eventual seeding of microorganisms. The angular blepharitis condition had persisted for a period of two years.

Physical Appearance of Affected Area: The skin of the temporal canthi of both eyes (outer angles where the lids meet) were red and inflamed with scaling present. Minute fissures and cracks were present in the skin at the temporal canthi and in the groove extending from the canthi of both eyes.

Prior Treatment: All treatments unsuccessful with the exception of steroids.

Treatment Regime: Emulsion formulation rubbed onto affected areas two to three times per day as required.

Results: Resolution in two to three weeks with almost all redness and inflammation resolved and scales absent.

EXAMPLE 3

Diagnosis: Pre-cancerous basal cell damage precluding the healing of affected area.

History: Basal cell compromise resulting from long-term sun exposure.

Physical Appearance of Affected Area: Persistent erythematous skin macules having a size of from 5–8 mm. located over the superior aspect of the zygomatic bone. The general area evidenced occasional and mild hemorrhaging.

Prior Treatment: Multiple commonly used creams were utilized for over 1 year. When condition did not resolve, Desowen steroid cream (0.05 %) was prescribed by dermatologist. Afflicted area never completely healed despite use 3 times per day for 3 months.

Treatment Regime: Cream formulation applied twice daily on affected area.

Results: No significant change first 6 days of application. Twenty percent improvement in redness by seventh day. Continuing improvement over a period of eight to fourteen days. By day twenty, the condition was ninety percent resolved.

EXAMPLE 4

Diagnosis: Eczema.

History: Recurrent tetter patch located over right thumb over the opponens pollicis. The condition occurred intermittently over a period of three years.

Physical Appearance of Affected Area: Hyperpigmentation, erythema, raised, scaly appearance. No oozing or seething. Subjective symptoms include burning and itching. Condition exacerbated by central heating.

Prior Treatment: Cortaid (OTC topical steroid) and other moisturizers for dry skin used. Steroid cream was found effective though other creams were found to be ineffective.

Treatment Regime: Cream formulation applied four times daily to affected area.

Results: Resolution of burning and itching within 24 hours. Erythema and hyperpigmentation markedly reduced after only 2 applications. Condition almost fully resolved after 4 days. Continued applications twice daily prevented recurrence.

EXAMPLE 5

Diagnosis: Chronically dry elbows.

History: Damaged epidermis due to dryness and exposure present for a period of about two years.

Physical Appearance of Affected Area: Red, tough (almost calloused) and fissured (cracked) epidermis corresponding to chronically exposed area on the elbow. Subjective symptoms of pain preventing leaning on the elbows.

Prior Treatment: Variety of dry skin creams mostly Eucerin at night.

Treatment Regime: Cream formulation applied four times daily on affected area for one week.

Results: No change first 2 days. Then surrounding skin became softer. At day 7, all redness resolved, the skin was no longer fissured and was soft to palpitation. One week after cessation of treatment, the condition recurred though to a lesser degree.

EXAMPLE 6

Diagnosis: Dry skin.

History: Back of heels exhibited chronic dryness and skin fissures. Additionally, severe skin peeling after sun exposure and razor burn on inner thighs after shaving. For a period of over ten years, the condition occurred annually from May through October.

Physical Appearance of Affected Area: Heels—Persistent rough, calloused and fissured condition on back of heels. Thighs exhibited tetters and razor burn after shaving. The sun caused a high degree of exfoliation all over body.

Prior Treatment: Mostly the more expensive brands of skin creams such as Elizabeth Grady, Lancome and Clinique.

Treatment Regime: Cream formulation applied twice daily for one week.

Results: Heels—redness gone within twenty-four hours. Skin soft and healed by day three of application. Thighs do not react after shaving when cream administered after showering. No peeling of skin after sun exposure on areas of skin to which cream had been applied.

EXAMPLE 7

Diagnosis: Marginal blepharitis.

History: Chronic problem since childhood associated with severe itching and discomfort. The condition persisted over a period of about twenty years.

Physical Appearance of Affected Area: Inflamed erythematous lid margins with scales and crusts on the eyelashes and on the lid margins.

Prior Treatment: Lid scrubs, OTC creams and steroid ointments prescribed by ophthalmologists.

Treatment Regime: Emulsion formulation applied three to four times per day.

Results: After three to four days, significant improvement was found. After ten days, examination revealed ninety percent of lid margins resolved with resolution dramatically superior to OTC cream therapy and equivalent to steroid therapy. Complete relief from itching and discomfort.

EXAMPLE 8

Diagnosis: Marginal blepharitis (Seborrheic).

History: Long-term problem of red erythematous eyelids and associated discomfort accompanied by eyes being chronically red lasting over a period of about ten years.

Physical Appearance of Affected Area: The lid margins were significantly inflamed with heavy scaling and crusts at the bases of the eyelashes and along the eyelashes. The lid margins were also involved with dilated vessels and scaling.

Prior Treatment: All contemporary treatments had been utilized including specialized lid scrub formulations. Steroids, which were prescribed by an ophthalmologist, were required to control this chronic condition of seborrheic marginal blepharatis.

Treatment Regime: Cream formulation applied three to four times per day.

Results: After one week, no significant improvement was observed. After two weeks, dramatic improvement of acute phase with resolution of redness of eyelids with no inflammation visible (dilated vessels over the eyelid margins remained as would be expected). The subjective symptoms were totally resolved.

EXAMPLE 9

Diagnosis: Severe recalcitrant eczema with lichenification and accentuation of skin markings.

History: A 33 year history of persistent whole body lichenification, scaling, erythematous fissured skin accompanied by severe itching. This condition was so severe that it requires hospitalization more than once per year.

Physical Appearance of Affected Area: Test area—anterior surface of leg (shin). Condition included symptoms of constant and severe itching, signs of severe scaling (exfoliation), erythema of skin, lichenification, and accentuation of skin markings. Condition was severe and steroids had been used so frequently that the skin had thinned.

Prior Treatments: Treatment regimens have included oral administration of systemic steroids (prednisone) and topical applications of cold tars, occlusive dressings and ointments.

Treatment Regime: Cream formulation applied twice daily for two weeks beginning.

Results: At two weeks following treatment, scales completely resolved. Skin was smooth and equivalent to skin over opposite leg simultaneously treated with steroid cream. Skin color and texture was unchanged. Accentuation of skin markings was unchanged. The symptom of itching had resolved over both legs.

EXAMPLE 10

Diagnosis: Localized eczema on arms, legs and neck.

History: Recurring eczema over a period of ten years on arms, legs and neck becoming worse in winter with dryness.

Physical Appearance of Affected Area: Typical scaly, wrinkled appearance with associated erythema (redness).

Prior Treatment: Usual treatments with non-steroidal cream medications with minimal success. Steroids effective when used but subject advised by dermatologist to use at a minimum only when required.

Treatment Regime: Cream formulation applied by rubbing onto the left arm on the left leg as needed up to six times per day. Right arm and leg treatment—the right arm and the right leg were treated by the same method with the subject's usual non-steroidal cream.

Results: Left arm and left leg—After two weeks, twenty five percent improved. After four weeks, seventy percent improved. Control—right arm and right leg treated with non-steroidal cream. Less than ten percent improvement observed after inspection following two weeks of treatment and again following four weeks of treatment.

EXAMPLE 11

Diagnosis: Localized psoriasis on arms.

History: A greater than 10 year history of recurring psoriasis over majority of body which was found to be particularly severe on the arms. The condition was more severe in winter than during other seasons.

Physical Appearance of Affected Area: Typical appearance of psoriasis with lesions, hyperemia and denuding of skin with small areas of vascular exposure.

Prior Treatment: Long history of treatment with non-steroidal cream, asteroid cream, plus several visits to hospital for tar treatment by dermatologist.

Treatment Regime: Cream formulation used on left arm up to six times per day as needed. Right arm treated with prior non-steroidal over the counter cream utilizing same methods and frequency as for left arm.

Results: Left arm with cream —after two weeks, thirty percent improved. After four weeks, fifty to seventy percent improved. Right arm with control cream—after two weeks, no significant improvement. After four weeks, a maximum of twenty five percent improvement.

EXAMPLE 12

Diagnosis: Localized facial and eyelid eczema below eyes.

History: Areas of eczema on upper malar skin surface areas below both eyes which was reported to be present for more than ten years. Condition exacerbates in winter and also when swimming in chlorinated pools.

Physical Appearance of Affected Area: Areas underneath both eyes approximately equal and approximately 40 mm. wide by 25 mm. high. Areas of eczema located directly below both eyes and eyelashes on external skin. Areas accompanied by skin erythema (redness) and patchy areas of desquamation and denudement. Small vesicles with crusting.

Prior Treatment: Treated by ophthalmologist with antibiotics and steroid creams. The condition was partially responsive to steroids.

Treatment Regime: Emulsion formulation applied and rubbed onto areas three times per day below left eye. Areas below right eye were treated with prior antibiotic medication as a control.

Results: After two weeks of treatment with emulsion, seventy five percent resolved. After four weeks, ninety percent resolved. Contralateral side treated with prior antibiotic medication exhibited no significant improvement after two weeks and only slight improvement after four weeks.

EXAMPLE 13

Diagnosis: Localized eczema on skin below eyes.

History: Areas of eczema on areas below both eyes which persisted for over five years.

Physical Appearance of Affected Area: Scaly, dry skin approximately 30 mm wide by 10 mm high complicated by erythema (redness) and patchy exposed areas of papules and vesicles with crusting.

Prior Treatment: Treatment by dermatologist with various antibiotic medications with only partial success.

Treatment Regime: Emulsion formulation was rubbed onto the affected areas of the left eyes two to three times daily as required. The areas underneath the right eye were treated with the previously used antibiotic medication, two to three times daily as a control utilizing the same frequency of application.

Results: Using emulsion, after one week, fifty percent resolution. After two weeks, seventy five percent resolution. After three weeks, eighty five percent resolution for left side. Right side treated with prior medication as control exhibited minimal improvement at two or three weeks though subject reported transient improvement from one day to another which then regressed.

We claim:

1. A method for treatment of human skin by enhancing formation of lamellae between corneocytes within the skin, said method comprising topical application of a pharmaceutically acceptable composition to the skin, said composition consisting of a carrier, an efficacious amount of a neutral oil and an efficacious amount of a bilayer component that is a mixture of a negatively charged phospholipid and a triglyceride.

2. The method of claim 1 where the phospholipid bilayer component conforms to the formula

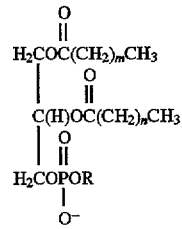

where m and n are whole integers varying between about 8 and 24 and R represents a moiety esterified to the phosphoric group, and the triglyceride conforms to the formula

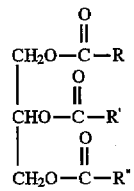

where each of R, R' and R" is a fatty acid residue having from 14 to 28 carbon atoms.

3. The method of claim 1 where the phospholipid is a phosphoglyceride.

4. The method of claim 1 where the phospholipid is selected from the group consisting of a phosphatidyl glycerol and phosphatidyl inositol.

5. The method of claim 1 where the phospholipid is dimyristylphosphatidylglycerol.

6. The method of claim 1 where the oil neutral is a non-polar oil.

7. The method of claim 6 where the neutral oil is mineral oil.

8. The method of claim 1 where the composition is in the form of a cream or a lotion.

9. The method of claim 8 where the composition is in the form of a cream.

10. The method of claim 1 where the composition contains a pharmacologically active agent.

11. The method of claim 2 where the concentration of the bilayer component varies between 0.1 and 30 percent by weight of the entire composition.

12. The method of claim 2 where the triglyceride is the product of reaction of glycerol with an organic acid selected from the group of myristic acid, palmitic acid, palmitoleic acid, stearic acid, oleic acid, linoleic acid, linolenic acid, ricinoleic acid, gadoleic acid, arachidonic acid, behenic acid, cetoleic acid and erucic acid.

13. The method of claim 2 where the concentration of the neutral oil varies between 0.1 and 35 percent by weight.

14. The method of claim 7 where the mineral oil is an n-alkane oil having form 14 to 26 carbon atoms.

15. The method of claim 2 where the concentration of the neutral oil varies between 0.1 and 35 percent by weight.

16. The method of claim 15 where the neutral oil is a non-polar oil.

17. The method of claim 15 where the neutral oil is mineral oil.

18. The method of claim 17 where the mineral oil is an n-alkane oil having form 14 to 26 carbon atoms.

* * * * *